(12) United States Patent
Ki et al.

(10) Patent No.: US 10,208,386 B2
(45) Date of Patent: Feb. 19, 2019

(54) HYDROGEN WATER MANUFACTURING SYSTEM

(71) Applicant: HUANTH CO., LTD., Gwangju-si, Gyeonggi-do (KR)

(72) Inventors: Byoung-Ho Ki, Seoul (KR); Choong-Choon Yu, Gwangju-si (KR)

(73) Assignee: HUANTH CO., LTD., Gwangju-si, Gyeonggi-Do (KR)

( * ) Notice: Subject to any disclaimer, the term of this patent is extended or adjusted under 35 U.S.C. 154(b) by 174 days.

(21) Appl. No.: 15/514,626

(22) PCT Filed: Oct. 19, 2015

(86) PCT No.: PCT/KR2015/011013
§ 371 (c)(1),
(2) Date: Mar. 27, 2017

(87) PCT Pub. No.: WO2016/076543
PCT Pub. Date: May 19, 2016

(65) Prior Publication Data
US 2017/0241024 A1 Aug. 24, 2017

(30) Foreign Application Priority Data

Nov. 10, 2014 (KR) .................. 10-2014-0155598

(51) Int. Cl.
*C02F 1/28* (2006.01)
*C02F 1/68* (2006.01)
(Continued)

(52) U.S. Cl.
CPC .............. *C25B 1/10* (2013.01); *C02F 1/4676* (2013.01); *C02F 1/46104* (2013.01); *C02F 1/68* (2013.01);
(Continued)

(58) Field of Classification Search
CPC ... C25B 1/10; C25B 9/08; C25B 15/08; C02F 1/4676; C02F 2201/46115; C02F 2209/42;
(Continued)

(56) References Cited

U.S. PATENT DOCUMENTS

2011/0198236 A1* 8/2011 Sumita ................ B01D 61/025
205/746
2012/0070540 A1* 3/2012 Igarashi .................... A23L 2/54
426/67

(Continued)

FOREIGN PATENT DOCUMENTS

JP          2006-263615 A     10/2006
KR   10-2009-0037231 A      4/2009
(Continued)

OTHER PUBLICATIONS

Search Report, dated Jan. 26, 2016, for International Application No. PCT/KR2051/011013.

*Primary Examiner* — Nicholas A Smith
(74) *Attorney, Agent, or Firm* — LRK Patent Law Firm

(57) ABSTRACT

A hydrogen water manufacturing system includes: a container-shaped constant pressure maintaining unit receiving water and maintaining a water level; an electrolysis unit including a hermetically sealed container bisected into an oxygen generation chamber and a hydrogen generation chamber with an ion exchange membrane interposed therebetween, wherein the chambers independently receive the raw water from the constant pressure maintaining unit, and a positive electrode plate is provided in the oxygen generation chamber and a negative electrode plate is provided in the hydrogen generation chamber; a fluid pump receiving the water and hydrogen from the hydrogen generation chamber; a dissolution unit having a nozzle to inject the water and the hydrogen supplied from the fluid pump; and (Continued)

a flow rate detection sensor arranged on piping downstream of the dissolution unit to detect supply of hydrogen water and drive the fluid pump and simultaneously supply electrical power to the electrolysis unit.

3 Claims, 4 Drawing Sheets

(51) Int. Cl.
    *C25B 1/10*     (2006.01)
    *C25B 9/08*     (2006.01)
    *C02F 1/461*     (2006.01)
    *C02F 1/467*     (2006.01)
    *C25B 15/08*     (2006.01)

(52) U.S. Cl.
    CPC ............... *C25B 9/08* (2013.01); *C25B 15/08* (2013.01); *C02F 1/283* (2013.01); *C02F 2201/4611* (2013.01); *C02F 2201/4612* (2013.01); *C02F 2201/4618* (2013.01); *C02F 2201/46115* (2013.01); *C02F 2201/46145* (2013.01); *C02F 2209/40* (2013.01); *C02F 2209/42* (2013.01); *Y02E 60/366* (2013.01)

(58) Field of Classification Search
    CPC ........ C02F 2204/40; C02F 2201/46145; C02F 2201/4618; C02F 1/46104
    See application file for complete search history.

(56) References Cited

U.S. PATENT DOCUMENTS

2013/0043124 A1*   2/2013   Park ..................... C02F 1/4676
                                                        204/263
2016/0032467 A1*   2/2016   Kim ........................ C25B 9/08
                                                        204/263
2017/0065940 A1*   3/2017   Mizutani .................. C02F 1/68

FOREIGN PATENT DOCUMENTS

| KR | 10-2010-0000454 A | | 1/2010 |
|---|---|---|---|
| KR | 10-2011-0019285 A | | 2/2011 |
| KR | 20110019285 A | * | 2/2011 |
| KR | 10-1071558 B1 | | 10/2011 |
| KR | 10-2013-0073831 A | | 7/2013 |
| KR | 10-2013-0085815 A | | 7/2013 |
| KR | 10-1427989 B1 | | 8/2014 |

* cited by examiner (a)

(b)

HYDROGEN WATER MANUFACTURING SYSTEM

CROSS-REFERENCE TO RELATED APPLICATION(S)

The present application is a U.S. National Phase entry from International Application No. PCT/KR2015/011013, filed Oct. 19, 2015, which claims priority to Korean Patent Application No. 10-2014-0155598, filed Nov. 10, 2014, the disclosure of which is incorporated by reference herein in its entirety.

BACKGROUND OF THE INVENTION

1. Field of the Invention

The present invention relates to a hydrogen water manufacturing system using electrolysis of water, and more particularly, to an apparatus configured such that there is no concern that ozone which may be generated during electrolysis may be contained in hydrogen water to be supplied, water pressure of raw water is prevented from acting on an electrolyzer which is a key component, and the amount of dissolved hydrogen in the hydrogen water s increased, thereby improving durability of various components, greatly increasing the amount of dissolved hydrogen in the hydrogen water, rapidly supplying the manufactured hydrogen water to maximize effects obtained by the hydrogen water, and preventing damage to the components that may result from unavoidable interruption of the supply of raw water.

2. Description of Related. Art

In general, hydrogen water refers to water in which hydrogen molecules ($H_2$) are mixed at a predetermined level or more, and it was published in the Journal of Nature Medicine in USA on May 8, 2007 that the hydrogen water has a therapeutic effect on cancer, brain disease and arteriosclerosis Upon drinking of the hydrogen water, the hydrogen water is effective for prevention of dermatitis such as atopic dermatitis, whitening of skin, prevention of aging through anti-oxidation, an increase in immunity, and the like. In particular, if radiation contaminants are introduced into a human body, active oxygen is increased to cause various diseases such as cancer. The hydrogen water has recently attracted attention because the drinking of the hydrogen water has an effect of removal of the active oxygen.

The hydrogen water with such various effects is usually manufactured through electrolysis or a chemical reaction using magnesium (Mg). Particularly, the hydrogen water has a disadvantage in that the hydrogen water should be drunk up within a short period of time after the manufacture thereof because a dissolved state of hydrogen in the hydrogen water is maintained for a short time, whereby it is difficult to distribute and supply the hydrogen water.

For this reason, apparatuses for directly manufacturing hydrogen water have recently been developed in various forms.

One example of conventional hydrogen water manufacturing apparatuses using electrolysis is disclosed in Korean Patent Laid-Open Publication No. 10-2013-73831.

In the conventional hydrogen water manufacturing apparatus disclosed in Korean Patent Laid-Open Publication No. 10-2013-73831, however, since after performing electrolysis in a container having a predetermined volume, a user drinks hydrogen water produced in this container, it is impossible to continuously produce the hydrogen water. In particular, there is concern that the amount of dissolved ozone harmful to a human body is increased in the hydrogen water produced through electrolysis.

Moreover, another example of conventional hydrogen water manufacturing apparatuses using electrolysis is disclosed in Korean Patent Laid-Open Publication No. 10-2013-85815.

The conventional hydrogen water manufacturing apparatus disclosed in Korean Patent Laid-Open Publication No. 10-2013-85815 also has problems that oxygen generated through the electrolysis is not treated separately, whereby there is great concern that the amount of dissolved ozone is increased in the produced hydrogen water, and that various components are directly exposed to raw water and pressure of the raw water is applied directly to these components, whereby durability of the components is deteriorated so that it is difficult to use the apparatus for a long period of time.

Additionally, a further example of conventional hydrogen water manufacturing apparatuses using electrolysis is disclosed in Korean Patent No. 10-1427989.

However, the conventional hydrogen water manufacturing apparatus disclosed in Korean Patent No. 10-1427989 has a conventional technical problem that hydrogen water generated through the electrolysis is simply supplied as it is, whereby there is a limitation on the amount of dissolved hydrogen in the hydrogen water.

SUMMARY OF THE INVENTION

The present invention is conceived to solve the aforementioned problems and is to provide a hydrogen water manufacturing system in which water pressure in a water-supply pipe is prevented from acting directly on various components in the hydrogen water manufacturing system, thereby improving durability of the various components, greatly increasing the amount of dissolved hydrogen in hydrogen water through dissolution of hydrogen in raw water by, a dissolution unit, rapidly supplying the manufactured hydrogen water to maximize effects obtained by the hydrogen water, and preventing damage to the components that may result from unavoidable interruption of the supply of raw water.

The present invention is achieved by a hydrogen water manufacturing system including a container-shaped constant pressure maintaining unit for receiving and storing raw water and maintaining a predetermined water level, an electrolysis unit composed of a hermetically sealed container bisected into an oxygen generation chamber and a hydrogen generation chamber with an ion exchange membrane interposed therebetween, wherein the chambers independently receive the raw water from the constant pressure maintaining unit, and a positive electrode plate is provided in the oxygen generation chamber and a negative electrode plate is provided in the hydrogen generation chamber to perform electrolysis in response to supply of electrical power; a fluid pump for receiving the raw water and hydrogen from the hydrogen generation chamber of the electrolysis unit and forcibly feed them; a dissolution unit having a nozzle to inject the raw water and the hydrogen supplied from the fluid pump, thereby dissolving the hydrogen in the raw water; and a flow rate detection sensor arranged on piping downstream of the dissolution unit so as to detect supply of hydrogen water and drive the fluid pump in response to the detection and simultaneously supply electrical power to the electrolysis unit to perform electrolysis.

It is preferable that the hydrogen water manufacturing system further includes an automatic shut-off valve provided between the constant pressure maintaining unit and piping disposed between the fluid pump and the dissolution unit to prevent damage to the fluid pump, wherein the automatic shut-off valve is opened at a pressure not greater than a predetermined pressure preset according to pressure in the piping so as to discharge air from the piping between the fluid pump and the dissolution unit into the constant pressure maintaining unit.

Moreover, it is most preferable that the dissolution unit includes the nozzle for injecting the raw water and the hydrogen in a vertically downward direction; a bowl shaped inner container having a plurality of through-holes formed in peripheral wall; and a casing for accommodating the inner container and having an upper portion where the nozzle is placed and a lower portion where an outlet is formed.

Advantageous Effects

The present invention can prevent water pressure in a water-supply pipe from acting directly on various components in a hydrogen water manufacturing system, thereby improving durability of the various components, greatly increasing the amount of dissolved hydrogen in hydrogen water through dissolution of hydrogen in raw water by a dissolution unit, rapidly supplying the manufactured hydrogen water to maximize effects obtained by the hydrogen water, and preventing damage to the components that may result from unavoidable interruption of the supply of raw water.

DETAILED DESCRIPTION OF THE INVENTION

Figure 1:
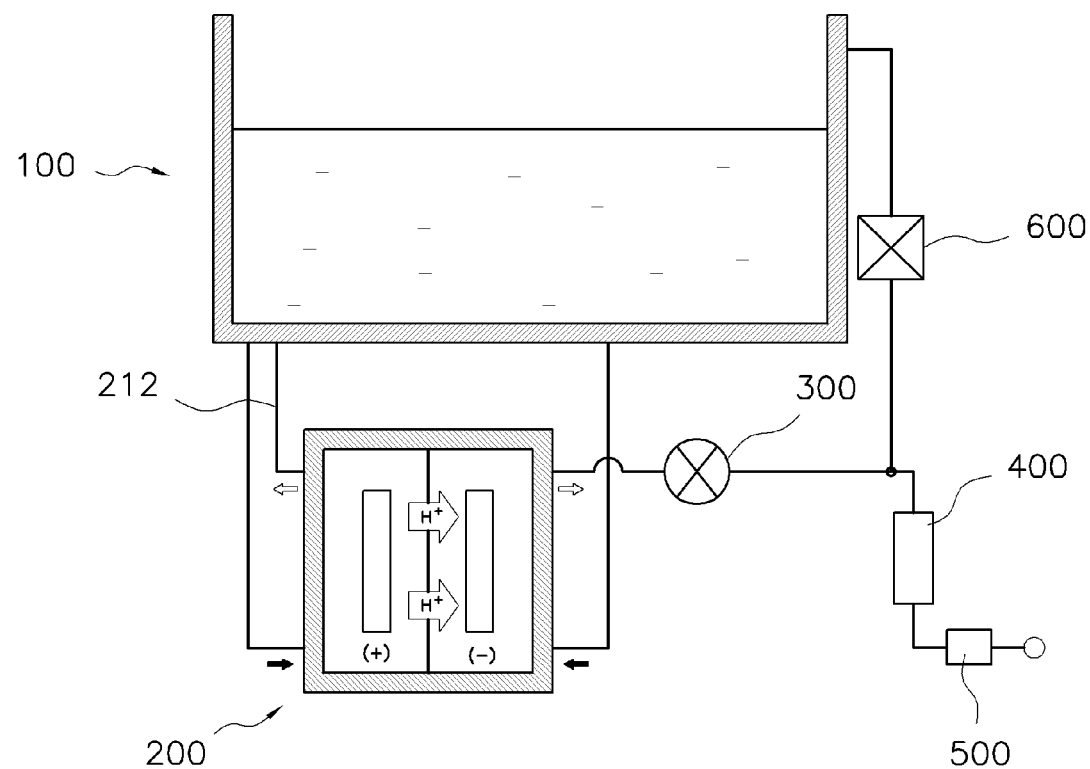
FIG. 1 is a schematic view illustrating, a configuration of a hydrogen water manufacturing system according to the present invention.
Figure 2:
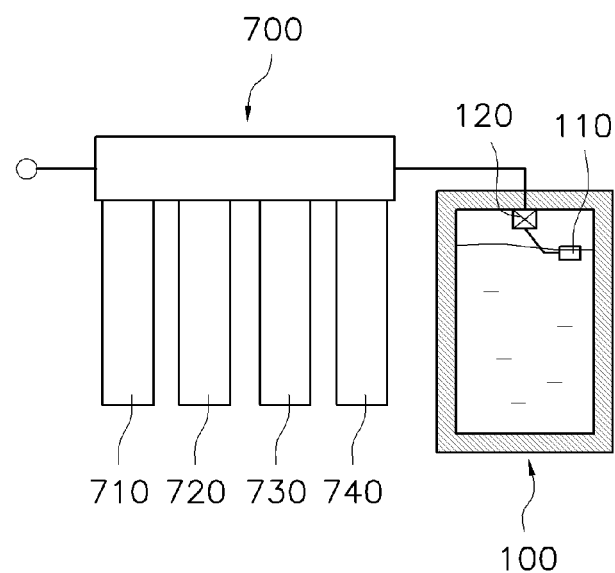
FIG. 2 is a sectional view illustrating an embodiment of a constant pressure maintaining, unit in a hydrogen water manufacturing system according to the present invention.
Figure 2:
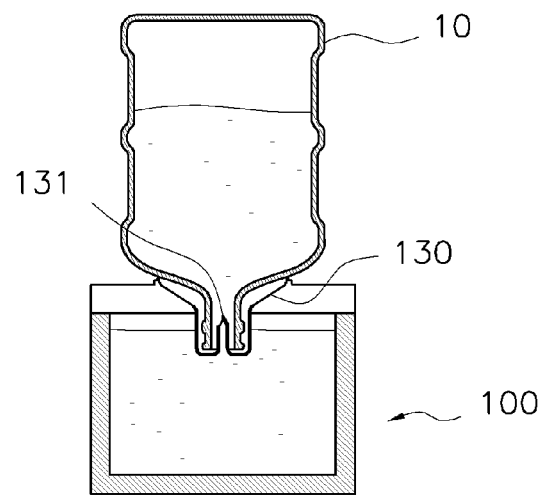

FIG. 1 is a schematic view illustrating a configuration of a hydrogen water manufacturing system according to the present invention. FIG. 2 is a sectional view illustrating an embodiment of a constant pressure maintaining unit in a hydrogen water manufacturing system according to the present invention, where (a) illustrates a direct-connection type constant pressure maintaining unit, and (b) illustrates a replaceable type constant pressure maintaining unit.

Figure 3:
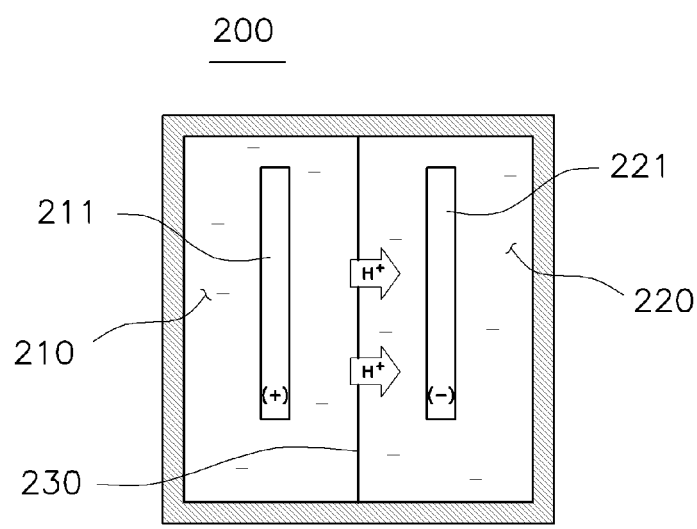
FIG. 3 is a sectional view illustrating an electrolysis unit in the hydrogen water manufacturing system according to the present invention.
Figure 4:
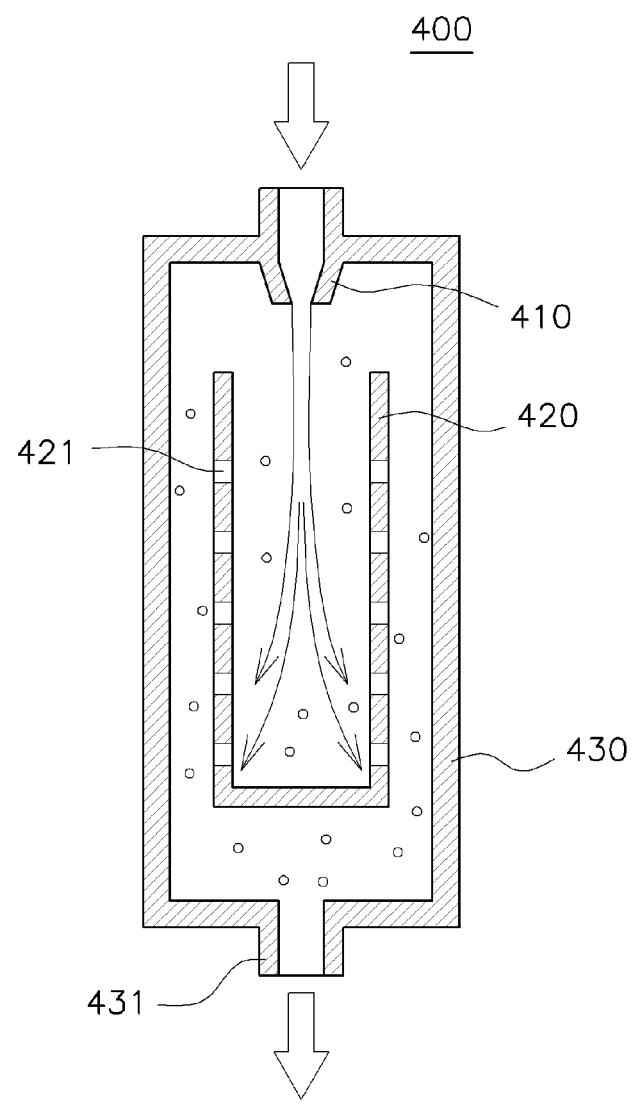
FIG. 4 is a sectional view illustrating a dissolution unit in the hydrogen water manufacturing system according to the present invention.

Moreover, FIG. 3 is a sectional view illustrating an electrolysis unit in the hydrogen water manufacturing system according to the present invention, and FIG. 4 is a sectional view illustrating a dissolution unit in the hydrogen water manufacturing system according to the present invention.

As shown in FIGS. 1 to 4, the hydrogen water manufacturing system according to the present invention is technically characterized by including a container-shaped constant pressure maintaining unit 100 for receiving and storing raw water and maintaining a predetermined water level; an electrolysis unit 200 composed of a hermetically sealed container bisected into an oxygen generation chamber 210 and a hydrogen generation chamber 220 with an ion exchange membrane 230 interposed therebetween, wherein the chambers independently receive the raw water from the constant pressure maintaining unit 100, and a positive electrode plate 211 is provided in the oxygen generation chamber 210 and a negative electrode plate 221 is provided in the hydrogen generation chamber 220 to perform electrolysis in response to supply of electrical power; a fluid pump 300 for receiving the raw water and hydrogen from the hydrogen generation chamber 220 of the electrolysis unit 200 and forcibly feed them; a dissolution unit 400 having a nozzle 410 to inject the raw water and the hydrogen supplied from the fluid pump 300, thereby dissolving the hydrogen in the raw water; and a flow rate detection sensor 500 arranged on piping downstream of the dissolution unit 400 so as to detect supply of hydrogen water and drive the fluid pump 300 in response to the detection and simultaneously supply electrical power to the electrolysis unit 200 to perform electrolysis.

Hereinafter, an embodiment of the present invention will be described below in detail with reference to the accompanying drawings.

As shown in FIGS. 1 to 4, the hydrogen water manufacturing system according to the present invention is composed of the constant pressure maintaining unit 100, the electrolysis unit 200, the fluid pump 300, the dissolution unit 400 and the flow rate detection sensor 500.

First of all, the constant pressure maintaining unit 100 is formed in, the shape of a container, and receives and stores the raw water and maintains a predetermined water level therein so that the raw water is supplied under a certain maintained pressure in the system.

This constant pressure maintaining unit 100 may be classified into a direct-connection type constant pressure maintaining unit and a replaceable type constant pressure maintaining unit depending on manners of supplying the raw water.

The direct-connection type constant pressure maintaining unit refers to a unit configured to be connected directly to piping such as a water pipe for supplying raw water, and the replaceable type constant pressure maintaining unit refers to a unit in which a predetermined cartridge type raw water reservoir 10 with raw water contained therein is repeatedly replaced.

In the direct-connection type constant pressure maintaining unit 100, a float 110 and an opening-closing valve 120 are provided therein such that the raw water can be stored at a predetermined water level in the constant pressure maintaining unit 100.

The float 110 and the opening-closing valve 120 are placed approximately at an upper portion of the constant pressure maintaining unit 100, so that when the float 110 is raised or lowered according to a water level of the raw water, the opening-closing valve 120 is opened or closed according to the raising or lowering of the float 110.

In other words, the opening-closing valve 120 is closed when the float 110 is raised above a predetermined height, and the opening-closing valve 120 is opened when the float 110 is lowered below the predetermined height.

Here, as for the opening-closing valve 120, there is no limitation on the type of the valve, and a needle valve is most preferable in the present invention.

In this manner, the raw water is always stored at a constant water level in the constant pressure maintaining unit 100, and as a result, water pressure acting on the piping for supplying the raw water such as a water pipe does not act on the constant pressure maintaining unit 100 as it is and can be maintained at a constant value.

In the direct-connection type constant pressure maintaining unit 100 described above, a preliminary filter unit 700 shown in (a) of FIG. 2 may be provided to supply purified raw water to the hydrogen water manufacturing system according to the present invention.

The preliminary filter unit 700 includes a plurality of filters connected to piping such as a water pipe, which receives raw water of a predetermined water pressure, and provided for filtering out foreign substances.

Depending on a required function, the filter provided in the preliminary filter unit 700 may consist of one or more combinations of a sediment filter for removing sand, soil, rust residue and the like; a pre-carbon filter for removing chlorine, trihalomethane, an odor and the like; a hollow fiber membrane filter for removing various heavy metal organic chemicals; a spiral wound type three-port membrane filter; and a post-carbon filter which improves taste of water and removes a gas or odor, and the like.

In the hydrogen water manufacturing system according to the present invention, it is preferable to sequentially provide four filters, i.e., a sediment filter 710, a pre-carbon filter 720, a hollow fiber membrane filter 730 and a post-carbon filter 740 in the preliminary filter unit 700.

Next, in case of the replaceable type constant pressure maintaining unit 100, as shown in (b) of FIG. 2, it is possible to mount a cartridge type raw water reservoir 10 having a predetermined shape and filled with raw water, whereby the raw water reservoir 10 is replaced with a new one when the raw water is exhausted.

To this end, a raw water reservoir mounting part 130 having a generally funnel-like shape is formed at an upper portion of the constant pressure maintaining unit 100 such that the cartridge type raw water reservoir 10 can be mounted in an inverted state.

A pointed portion 131 may be uprightly formed at a central floor surface of the raw water reservoir mounting part 130. When the cartridge type raw water reservoir 10 is turned upside down and a mouth of the raw water reservoir is inserted into the raw water reservoir mounting part 130, the pointed portion 131 may penetrate a sealing cover (not shown) for sealing the mouth of the cartridge type raw water reservoir 10 to allow the mouth to be opened.

Accordingly, the state where the raw water is always stored at a constant water level in the constant pressure maintaining unit 100 by the raw water supplied from the cartridge type raw water reservoir 10 is maintained, and as a result, water pressure can be consistently maintained in the constant pressure maintaining unit.

Subsequently, as shown in FIG. 3, the electrolysis unit 200 is composed of a sealed container bisected by the ion exchange membrane 230 so that an inside of the electrolysis unit 200 is divided into the oxygen generation chamber 210 and the hydrogen generation chamber 220.

Piping is provided to enable the oxygen generating chamber 210 and the hydrogen generation chamber 220 to independently receive the raw water from the constant pressure maintaining unit 100, as shown in FIG. 1.

Furthermore, the positive electrode plate 211 for the electrolysis is disposed in the oxygen generation chamber 210 of the electrolysis unit 200 and the negative electrode plate 221 for the electrolysis is disposed in the hydrogen generation chamber 220 so that when electric power is supplied to the positive electrode plate 211 and the negative electrode plate 221, water electrolysis is performed for the raw water.

In particular, the ion exchange membrane 230 that separates the oxygen generation chamber 210 and the hydrogen generation chamber 220 in the electrolytic unit 200 is a membrane which blocks movement of the water while allowing positive ions to be freely moved therethrough. It would be preferable to employ Nafion membrane available from DuPont as the ion exchange membrane in this embodiment.

As a result, when the electrolysis is performed in the electrolysis unit 200, oxygen is generated in the oxygen generation chamber 210 and hydrogen is generated in the hydrogen generation chamber 220.

It is preferable that as shown in FIG. 1, a separate return piping line 212 is formed at an upper portion of the oxygen generating chamber 210 so that the oxygen generated by the electrolysis can be returned to the constant pressure maintaining unit 100.

In this manner, the oxygen generated in the oxygen generating chamber 210 of the electrolysis unit 200 during the electrolysis is delivered to the constant pressure maintaining unit 100 through the return piping line 212 and is then discharged to the atmosphere. Additionally, if ozone is generated, it can also serve as an agent for sterilizing/disinfecting bacteria that may be produced in the constant pressure maintaining unit 100.

Moreover, the hydrogen generated in the hydrogen generating chamber 220 is partially dissolved in the raw water to generate hydrogen water with a relatively small amount of dissolved hydrogen, and this hydrogen water along with the raw water and the hydrogen are supplied to the fluid pump 300, as shown in FIG. 1.

The fluid pump 300 functions to receive the hydrogen water, the raw water and the hydrogen from the hydrogen generation chamber 220 of the electrolysis unit 200 and to forcibly feed them. Whether the fluid pump 300 is operated or not will be controlled by the flow rate detection sensor 500 to be described later.

The hydrogen water, the raw water and the hydrogen forcibly fed by the fluid pump 300 are directly supplied to the dissolution unit 400.

However, a filter unit (not shown) may be additionally provided between the fluid pump 300 and the dissolution unit 400. Such a filter unit can receive the raw water, the hydrogen and the hydrogen water with a relatively small amount of dissolved hydrogen, and filter them with an activated carbon filter, thereby eliminating a foreign substance and an odor produced by ozone.

Next, the dissolution unit 400 is configured to further dissolve the hydrogen in the raw water by means of high-pressure injection of the raw water and the hydrogen into a predetermined space through the nozzle 410. While the hydrogen water passes through the dissolution unit 400, it has a greatly increased amount of dissolved hydrogen in the hydrogen water.

This dissolution unit 400 may be employed in various forms having the nozzle 410. In particular, as shown in FIG. 4, it will be preferable that the dissolution unit 400 in the present invention is composed of the nozzle 410 for injecting the raw water and the hydrogen in a vertically downward direction; a bowl-shaped inner container 420 having a plurality of through-holes 421 formed in a peripheral wall; and a casing 430 that accommodates the inner container 420 and has an upper portion where the nozzle 410 is placed and a lower portion where an outlet 431 is formed.

In other words, the dissolution unit 400 is composed of the cylindrical casing 430 having an inlet formed at the upper portion and the outlet 431 formed at the lower portion so that the raw water, the hydrogen and the hydrogen water with a relatively small amount of dissolved hydrogen are injected downwardly by the nozzle 410 placed at the inlet and then collide with the inner container 420 having the plurality of through-holes 421 formed therein to enable much more hydrogen to be dissolved in the raw water.

As a result, hydrogen water with a relatively large amount of dissolved hydrogen is generated in the dissolution unit 400, and the hydrogen water in the dissolution unit 400 will be then supplied to a user through the flow rate detection sensor 500.

The flow rate detection sensor 500 is provided on piping downstream of the dissolution unit 400 to detect whether the hydrogen water is supplied or not.

The flow rate detection sensor 500 functions to operate the fluid pump 300 and to supply electrical power to the electrolysis unit 200 so as to perform electrolysis when the flow rate detection sensor 500 detects supply of the hydrogen water.

In other words, whether the fluid pump 300 is operated or not, and the electrolysis performed in the electrolysis unit 200 are determined based on whether the supply of the hydrogen water is detected or not by means of the flow rate detection sensor 500. As a result, it is possible to prevent unnecessary electrical power consumption and to generate and supply the hydrogen water in real time when a user utilizes the hydrogen water, without pre-generating the hydrogen water having an extremely short time during which the hydrogen has been dissolved.

Furthermore, although the configuration in which the oxygen generated during the electrolysis is delivered to the constant pressure maintaining unit 100 through the return piping line 212 and is then discharged to the atmosphere has been described above, this system may be employed to manufacture oxygen water by reversely disposing the electrodes in the electrolysis unit 200, if necessary, Hereinbefore, the generation of hydrogen water performed when the raw water is consistently and normally supplied to the constant pressure maintaining unit 100 in the hydrogen water manufacturing system of the present invention has been basically described. Now, prevention of damage that may occur in components of the hydrogen manufacturing system of the present invention, for example, when the raw water is not stored at a predetermined water level in the constant pressure maintaining unit 100 due to temporary cut off of a water supply or lack of timely replacement of the cartridge type raw water reservoir 10 will be described.

In other words, if the supply of the raw water through the constant pressure maintaining unit 100 is not smooth in the present invention, the electrolysis in the electrolysis unit 200 is not smoothly performed. Particularly, as the fluid pump 300 is filled with air, the fluid pump 300 idles accordingly, resulting in concern about damage to the fluid pump 300.

To this end, it is preferable in the present invention that an automatic shut-off valve 600 is additionally provided between the constant pressure maintaining unit 100 and the piping disposed between the fluid pump 300 and the dissolution unit 400 to prevent damage to the fluid pump 300, wherein the automatic shut-off valve 600 is opened at a pressure not greater than a predetermined pressure preset according to pressure in the piping so as to discharge air from the piping between the fluid pump 300 and the dissolution unit 400 into the constant pressure maintaining unit 100.

For example, when the raw water is appropriately supplied from the constant pressure maintaining unit 100, the fluid pump 300 pressurizes the raw water, the hydrogen and the hydrogen water with a relatively small amount of dissolved hydrogen so as to normally forcibly feed them to the dissolution unit 400.

Accordingly, a normal pressure greater than the preset predetermined pressure is applied to the automatic shut-off valve 600 connected between the constant pressure maintaining unit 100 and the piping disposed between the fluid pump 300 and the dissolution 400, and as a result, the automatic shut-off valve 600 is continuously maintained in a closed state so that the generation of the hydrogen water described above is normally performed.

However, when the raw water is not properly supplied from the constant pressure maintaining unit 100, most of an inside of the fluid pump 300 is filled with air so that there is concern that the fluid pump 300 idles.

In this case, a pressure not greater than the preset predetermined pressure acts on the automatic shut-off valve 600, and as a result, the automatic shut-off valve 600 is switched from the closed state into the opened state to discharge air in the piping between the fluid pump 300 and the dissolution unit 400 to the constant pressure maintaining unit 100.

In this manner, after the air in the piping between the fluid pump 300 and the dissolution unit 400 is completely discharged, a proper level of pressure is applied again, so that the automatic shut-off valve 600 is switched to the closed state again. With the automatic shut-off valve 600 that is additionally provided, the hydrogen water manufacturing system of the present invention can prevent damage to components, particularly damage to the fluid pump 300 that may occur because the raw water is not continuously supplied from the constant pressure maintaining unit 100.

Hereinafter, the operation of the present invention will be described with reference to FIGS. 1 to 4.

The constant pressure maintaining unit of the hydrogen water manufacturing system according to the present invention configured as described above may be classified into the direct-connection type constant pressure maintaining unit 100 and the replaceable type constant pressure maintaining unit 100 depending on manners of supplying the raw water. First, in case of the hydrogen water manufacturing system provided with the direct-connection type constant pressure maintaining unit 100, the raw water is supplied to the preliminary filter unit 700 via piping such as a water pipe and sequentially passes through the sediment filter 710, the pre-carbon filter 720, the hollow fiber membrane filter 730 and the post-carbon filter 740 so that filtration of the raw water may be performed.

The raw water filtered through the preliminary filter unit 700 is supplied to the constant pressure maintaining unit 100 and is stored at a certain water level in the constant pressure maintaining unit 100 by the float 110 and the opening-closing valve 120. If the water level of the raw water is lowered in response to supply of hydrogen water, the constant pressure maintaining unit 100 receives the raw water filtered through the preliminary filter unit 700 again.

In this manner, water pressure acting on the water pipe or the like is applied only upstream of the constant pressure maintaining unit 100, separate water pressure is not applied downstream of the constant pressure maintaining unit 100 and the supply of the hydrogen water is performed only by the fluid pump 300 downstream of the constant pressure maintaining unit 100, thereby preventing deterioration of durability or the like that may be occur if the water pressure acting on the water pipe is applied to an inside of the system.

Furthermore, in case of the replaceable type constant pressure maintaining unit 100, the raw water reservoir mounting part 130 in which the replaceable cartridge type raw water reservoir 10 can be mounted is formed, so that as the cartridge type raw water reservoir 10 is replaced with a new one, the constant pressure maintaining unit 100 always, maintains the state where the raw water is stored at a predetermined water level, and as a result, a constant water pressure can also be maintained.

Thereafter, the oxygen generation chamber 210 and the hydrogen generation chamber 220 are separated from each other in the sealed container of the electrolysis unit 200 by the ion exchange membrane 230, so that during the electrolysis, the oxygen is generated on the positive electrode plate 211 in the oxygen generation chamber 210 and the hydrogen is generated on the negative electrode plate 221 in the hydrogen generation chamber 220.

The oxygen generated in the oxygen generation chamber 210 may be delivered to the constant pressure maintaining unit 100 via the return piping line 212 provided on an upper side of the electrolysis unit 200, and then discharged to the atmosphere.

Since only positive ions can pass and move through the ion exchange membrane 230 and the water cannot move within the electrolysis unit 200 during the electrolysis, the hydrogen water generated in the hydrogen generation chamber 220 is not affected by the oxygen at all, so that it is possible to reliably prevent ozone or the like from being dissolved in the hydrogen water.

In this way, the raw water and the hydrogen are delivered to the dissolution unit 400 through the fluid pump 300 along with the hydrogen water having a relatively small amount of dissolved hydrogen generated in the hydrogen generation chamber 220 of the electrolysis unit 200.

Addition of a filter unit (not shown) enables an activated carbon filter to eliminate an odor contained in the hydrogen water and to additionally filter out foreign substances.

Next, the raw water and the hydrogen are strongly injected into the inner container 420 within the casing 430 by the nozzle 410 in the dissolution unit 400, so that hydrogen water with a relatively large amount of dissolved hydrogen may be generated in the dissolution unit 400 and the hydrogen water manufactured as such is supplied to a user through the flow rate detection sensor 500.

The flow rate detection sensor 500 detects the supply of the hydrogen water required by the user and controls the operation of the fluid pump 300 as well as the electrolysis of the electrolysis unit 200.

In this manner, the electrolysis and the operation of the fluid pump 300 are performed only when the user requires the supply of the hydrogen water, thereby enabling quick generation and supply of the hydrogen water without unnecessary power consumption.

Therefore, the hydrogen water manufacturing system of the present invention has an advantage that water pressure acting on a water pipe is not applied to an inside of the system, thereby preventing deterioration of durability of components which may be caused by water pressure.

Furthermore, since the inside of the electrolysis unit 200 is completely separated by the ion exchange membrane 230, the hydrogen water generated through the electrolysis is not affected by the oxygen at all, so that there is no concern about generation of ozone harmful to a human body.

Moreover, the high-pressure injection of the raw water and the hydrogen in the dissolution unit 400 can greatly improve the amount of dissolved hydrogen in the hydrogen water so as to supply higher-quality hydrogen water.

In addition to the foregoing, the present invention has excellent advantages that the electrolysis and the operation of the fluid pump 300 are performed by the flow rate detection sensor 500 to prevent unnecessary power consumption, and the hydrogen water is supplied within a short time after manufacture of the hydrogen water so that the hydrogen water with more hydrogen dissolved therein can be supplied to a user.

Above all, the present invention has an advantage that the addition of the automatic shut-off valve 600 prevents damage to the fluid pump 300 that may occur because the raw water is not smoothly supplied The embodiment is an example specifically illustrating the technical spirit of the present invention, and the scope of the present invention is not limited to the embodiment and the accompanying drawings.

What is claimed is:

1. A hydrogen water manufacturing system comprising:
 a container-shaped constant pressure maintaining unit for receiving and storing raw water and maintaining a predetermined water level;
 an electrolysis unit composed of a hermetically sealed container bisected into an oxygen generation chamber and a hydrogen generation chamber with an ion exchange membrane interposed therebetween, wherein the chambers independently receive the raw water from the constant pressure maintaining unit, and a positive electrode plate is provided in the oxygen generation chamber and a negative electrode plate is provided in the hydrogen generation chamber to perform electrolysis in response to supply of electrical power;
 a fluid pump for receiving the raw water and hydrogen from the hydrogen generation chamber of the electrolysis unit and forcibly feed them;
 a dissolution unit having a nozzle to inject the raw water and the hydrogen supplied from the fluid pump, thereby dissolving the hydrogen in the raw water; and
 a flow rate detection sensor arranged on piping downstream of the dissolution unit so as to detect supply of hydrogen water and drive the fluid pump in response to the detection and simultaneously supply electrical power to the electrolysis unit to perform electrolysis.

2. The hydrogen water manufacturing system of claim 1, further comprising an automatic shut-off valve provided between the constant pressure maintaining unit and piping disposed between the fluid pump and the dissolution unit to prevent damage to the fluid pump,
 wherein the automatic shut-off valve is opened at a pressure not greater than a predetermined pressure preset according to pressure in the piping so as to discharge air from the piping between the fluid pump and the dissolution unit into the constant pressure maintaining unit.

3. The hydrogen water manufacturing system of claim 2, wherein the dissolution unit comprises:
 the nozzle for injecting the raw water and the hydrogen in a vertically downward direction;
 a bowl-shaped inner container having a plurality of through-holes formed in a peripheral wall; and
 a casing for accommodating the inner container and having an upper portion where the nozzle is placed and a lower portion where an outlet is formed.

\* \* \* \* \*